US00RE43960E

(19) United States
(12) Reissued Patent
Barolak

(10) Patent Number: US RE43,960 E
(45) Date of Reissued Patent: Feb. 5, 2013

(54) SYSTEM FOR MEASURING STRESS IN DOWNHOLE TUBULARS

(75) Inventor: Joseph Gregory Barolak, Spring, TX (US)

(73) Assignee: Baker Hughes Incorporated, Houston, TX (US)

(21) Appl. No.: 13/079,546

(22) Filed: Apr. 4, 2011

Related U.S. Patent Documents

Reissue of:
(64) Patent No.: 7,660,197
Issued: Feb. 9, 2010
Appl. No.: 11/622,101
Filed: Jan. 11, 2007

(51) Int. Cl.
*G01V 1/40* (2006.01)
(52) U.S. Cl. ..... 367/35; 181/105
(58) Field of Classification Search ..... 367/35; 181/105
See application file for complete search history.

(56) References Cited

U.S. PATENT DOCUMENTS

| | | | | |
|---|---|---|---|---|
| 4,402,068 | A * | 8/1983 | Angehrn | 367/35 |
| 4,593,568 | A | 6/1986 | Telford et al. | 73/623 |
| 4,708,204 | A | 11/1987 | Stroud | 166/255 |
| 4,827,457 | A * | 5/1989 | Seeman et al. | 367/27 |
| 5,197,038 | A * | 3/1993 | Chang et al. | 367/30 |
| 5,503,020 | A | 4/1996 | Mandracchia | |
| 6,098,021 | A * | 8/2000 | Tang et al. | 702/14 |
| 7,660,197 | B2 * | 2/2010 | Barolak | 367/35 |
| 2005/0205268 | A1 * | 9/2005 | Engels et al. | 166/381 |
| 2005/0224229 | A1 * | 10/2005 | Blacklaw | 166/250.01 |

FOREIGN PATENT DOCUMENTS

| | | | |
|---|---|---|---|
| EP | 1020716 | A2 | 7/2000 |
| EP | 1467060 | A1 | 10/2004 |
| WO | WO2004106913 | A1 | 12/2004 |

OTHER PUBLICATIONS

Innerspec Technologies, EMAT Technology, http://www.innerspec.com/site/emat.asp, Oct. 10, 2006, pp. 1-2.
NDT Resource Center, Pulser-Receivers, http://www.ndt-ed.org/EducationResources/CommunityCollege/Ultrasonics/ . . . Oct. 5, 2006, pp. 1-2.
NDT Resource Center, Ultrasonic Measurement of Stress, http://www.ndt-ed.org/EducationResources/CommunityCollege/Ultrasonics/ . . . Oct. 5, 2006, pp. 1-2.
NDT Resource Center, Electromagnetic Acoustic Transducers (EMATs), http://www.ndt-ed.org/EducationResources/CommunityCollege/Ultrasonics/ . . . Oct. 5, 2006, pp. 1-2.
NDT Resource Center, Precision Velocity Measurements, http://www.ndt-ed.org/EducationResources/CommunityCollege/Ultrasonics/ . . . Oct. 5, 2006, pp. 1-2.
Cantrell, Jr. et al.; *Relative Slope Invariance of Velocity-Stress and Strain-Stress Curves*, 1981 Ultrasonics Symposium, pp. 434-437, 1 Fig., 1 Table.
Frankel et al.; *Residual Stress Measurement in Circular Steel Cylinders*, 1983 Ultrasonics Symposium, pp. 1009-1012, 3 Figs.

* cited by examiner

*Primary Examiner* — Ian Lobo
(74) *Attorney, Agent, or Firm* — Mossman Kumar & Tyler PC

(57) ABSTRACT

An apparatus for evaluating a tubular in a borehole of includes at least two electromagnetic acoustic transducers. The transducers are configured to generate and receive first and second acoustic waves in the tubular. A difference in velocity of the two acoustic waves is indicative of a stress field in the tubular.

38 Claims, 4 Drawing Sheets

SYSTEM FOR MEASURING STRESS IN DOWNHOLE TUBULARS

Matter enclosed in heavy brackets [ ] appears in the original patent but forms no part of this reissue specification; matter printed in italics indicates the additions made by reissue.

BACKGROUND OF THE INVENTION

1. Field of the Invention

The present disclosure provides an apparatus and method for testing the structural integrity of tubing and casings used in a borehole. In particular, the present disclosure discusses an apparatus and method using ultrasonic waves to estimate the stress on tubulars in a borehole environment.

2. Description of the Related Art

The environmental conditions encountered by production casing and tubing used in hydrocarbon recovery can result in stress buildup in the tubing. This stress in the tubing may come from pressure and temperature variations during production, movement of the formation due to pressure depletion, "flow" of salt formations, etc. This stress may eventually lead to casing or tubing collapse or shear, rendering the well inoperable. Prior art methods have generally involved waiting for the buildup of this stress to a point where mechanical deformation occurs before the stress can be detected.

Stress buildup may also occur in a drillstring during the drilling of a borehole. During drilling operations, it is not uncommon for the drillstring to get stuck. To recover the stuck pipe, it is first required to determine the upper most 'free' point of the drillpipe. This is done by measuring the torque and/or pull induced from the surface or the physical stretching of the drillpipe due to this torque or pull.

Stress in a casing or tubing may be in the form of an axial load, circumferential torque, or a bending moment. Although stresses are applied on the drilling equipment while in use in the borehole environment, testing for wear typically occurs uphole or in a laboratory, often by observing the residual stress on the mandrel from its use. In general, when a stress is applied to a material and then removed, a residual stress remains on the material. This residual stress is often observed by checking for atomic dislocations at the crystalline level of the material and can be used to determine properties related to the structural integrity of the material. Various methods have been designed to observe residual stress on materials, including X-ray diffraction techniques, determining magnetic permeability, and ultrasonic testing.

Changes in ultrasonic wave propagation speed, along with energy losses from interactions with materials microstructures are often used to nondestructively gain information about properties of the material. An ultrasonic wave may be created in a material sample, such as a solid beam, by creating an impulse at one region of the sample. As the wave propagates through the sample, stresses and other material changes or defects affect the wave. Once the affected wave is recorded, the nature of the stresses of the material can be determined. Measurements of sound velocity and ultrasonic wave attenuation can be related to the elastic properties that can be used to characterize the texture of polycrystalline metals.

Velocity measurements are of interest in longitudinal waves propagating in gases, liquids, and solids. In solids, transverse (shear) waves are also of interest. The velocity of a longitudinal wave is independent of a sample's geometry when the dimensions at right angles to the sample are large compared to the sample area and to the wavelength. The velocity of a transverse wave is affected little by the physical dimensions of the sample. The relationship between stress and velocity has been discussed for example by Cantrell and Chern, "Relative Slope Invariance of Velocity-Stress and Strain-Stress Curves," Ultrasonics Symposium, 1981.

Measurement of ultrasonic velocity is performed by measuring the time it takes for a pulse of ultrasound to travel from one transducer to another (pitch-catch scenario) or return to the same transducer (pulse-echo scenario). Another measurement method compares the phase of the detected sound wave with that of a reference signal, wherein slight changes in the transducer separation are seen as slight phase changes, from which the sound velocity can be calculated. These methods are suitable for estimating acoustic velocity to about 1 part in 100. Standard practice for measuring velocity in materials is detailed in American Society for Testing and Materials (ASTM) Publication E494. Residual stress measurements in cylinders have been discussed for example by Frankel et al., "Residual Stress Measurement in Circular Steel Cylinders," Ultrasonics Symposium, 1983.

An oriented measurement of magnetic permeability has also been used to determine stress. Several patents discuss the use of magnetic permeability to measure stress. U.S. Pat. No. 4,708,204 to Stroud discusses a system for determining the stuck point of pipe in a borehole including a wireline tool having an exciter coil and a receiver coil axially spaced from one another. The exciter coil is driven at a pre-selected low frequency and the voltage induced into the receiver coil is related to the magnetic permeability of a pipe through which the tool is run. A receiver coil voltage log is run of the section of pipe in the region of the stuck point first while that region is substantially free of mechanical stress. A second log of the same region is run with the pipe under mechanical stress. Comparison of the two logs determines the stuck point from the difference in magnetic permeability of the stressed pipe above the stuck point and the unstressed pipe below the stuck point.

European Patent Application EP 1 647 669 A1 discusses a method and apparatus for determining a stuck pipe. In one embodiment, a free point logging tool, having a freepoint sensor and, optionally, an acoustic sensor, is attached to a working line such as a wireline. The freepoint sensor acquires magnetic permeability data in a string of pipe, while the acoustic sensor acquires acoustic data in the pipe. Two sets of data for each sensor are acquired: one in which the pipe is unstressed, and one in which the pipe is stressed. The first set and second sets of magnetic permeability data are compared to determine the stuck point location of the pipe. The first and second sets of acoustic data are compared to determine the matter in which the pipe is stuck. EP 1 647 669 A1 references the use of travel time to measure stress but anticipates only a measure of axial travel time.

In petroleum exploration, time spent raising and lowering a drilling apparatus from and into a borehole is time that could otherwise be used in exploration and is thus costly. Historically, stress on a tubular containing drilling equipment used in a borehole has only been determined by looking for actual physical movement of the tubular (i.e., freepoint indicators) or by physical distortion of the tubular (i.e., casing inspection). Thus, it is desirable to perform stress testing of a drilling apparatus obtaining measurements downhole.

SUMMARY OF THE INVENTION

One embodiment of the invention is an apparatus for evaluating a tubular within a borehole. The apparatus includes a plurality of acoustic transducers configured to generate and receive first and second acoustic waves in the tubular. The first and second acoustic waves differ from each other in a direction of propagation and/or a direction of polarization. The apparatus further includes a processor configured to determine from the velocity of the first acoustic wave and the velocity of the second acoustic wave an indication of stress in the tubular. The acoustic transducers may include electromagnetic acoustic transducers, piezoelectric transducers, and/or wedge transducers. The acoustic transducers may be disposed on at least one pad extending from a body of for logging tool. The at least one pad may include a plurality of pads. The first and second acoustic waves may include a horizontally polarized shear wave and a vertically polarized shear wave propagating in the same direction. The indicator may be related to a torque, an axial stress, a bending load, a crushing load, corrosion of the tubular, and a mechanical defect in the tubular. The apparatus may further include a conveyance device used for conveying the logging tool into the borehole. The conveying device may be selected from a wireline, a drilling tubular, a slickline, and/or coiled tubing. The tubular may be production tubing, casing, and/or a drilling tubular.

Another embodiment of the invention is a method of evaluating a tubular within a borehole. The method includes propagating first and said second acoustic waves in the tubular. The second acoustic wave differs from the first acoustic wave in a direction of propagation and/or a direction of polarization. The method further determines from the velocity of the first acoustic wave and the velocity of the second acoustic wave an indication of the stress field in the tubular. The first and second acoustic waves may be generated using a plurality of acoustic transducers positioned on at least one pad extendable from a body of a logging tool. The first acoustic wave may include a horizontally polarized shear wave and the second acoustic wave may include a vertically polarize shear wave propagating in the same direction as the horizontally polarized shear wave. The indicator may be related to a torque, an axial stress, a bending load, a crushing load, corrosion, and a mechanical defect in the tubular. The method may further include conveying the logging tool into the borehole using a conveyance device that may be a wireline, a drilling tubular, a slickline, and/or coiled tubing. The tubular may be a production tubing, a casing, and/or a drillstring.

Another embodiment of the invention is a computer-readable medium for use with an apparatus for evaluating a tubular within a borehole. The apparatus includes a plurality of acoustic transducers configured to propagate and receive first and second acoustic waves in the tubular. The first acoustic wave and the second acoustic wave differ in at least one of a directional propagation, and a direction of polarization. The medium includes instructions which enable a processor to determine from the velocity of the first acoustic wave and the velocity of the second acoustic wave an indication of a stress in the tubular. The medium may include a ROM, an EPROM, and EEPROM, a flash memory and/or an optical disk.

BRIEF DESCRIPTION OF THE DRAWINGS

For a detailed understanding of the present invention, reference should be made to the following detailed description of the invention, taken in conjunction with the accompanying drawing and in which.

DETAILED DESCRIPTION OF THE INVENTION

The present invention is discussed with reference to specific logging instruments that may form part of a string of several logging instruments for conducting wireline logging operations. It is to be understood that the choice of the specific instruments discussed herein is not to be construed as a limitation and that the method of the present invention may also be used with other logging instruments as well.

Figure 1:
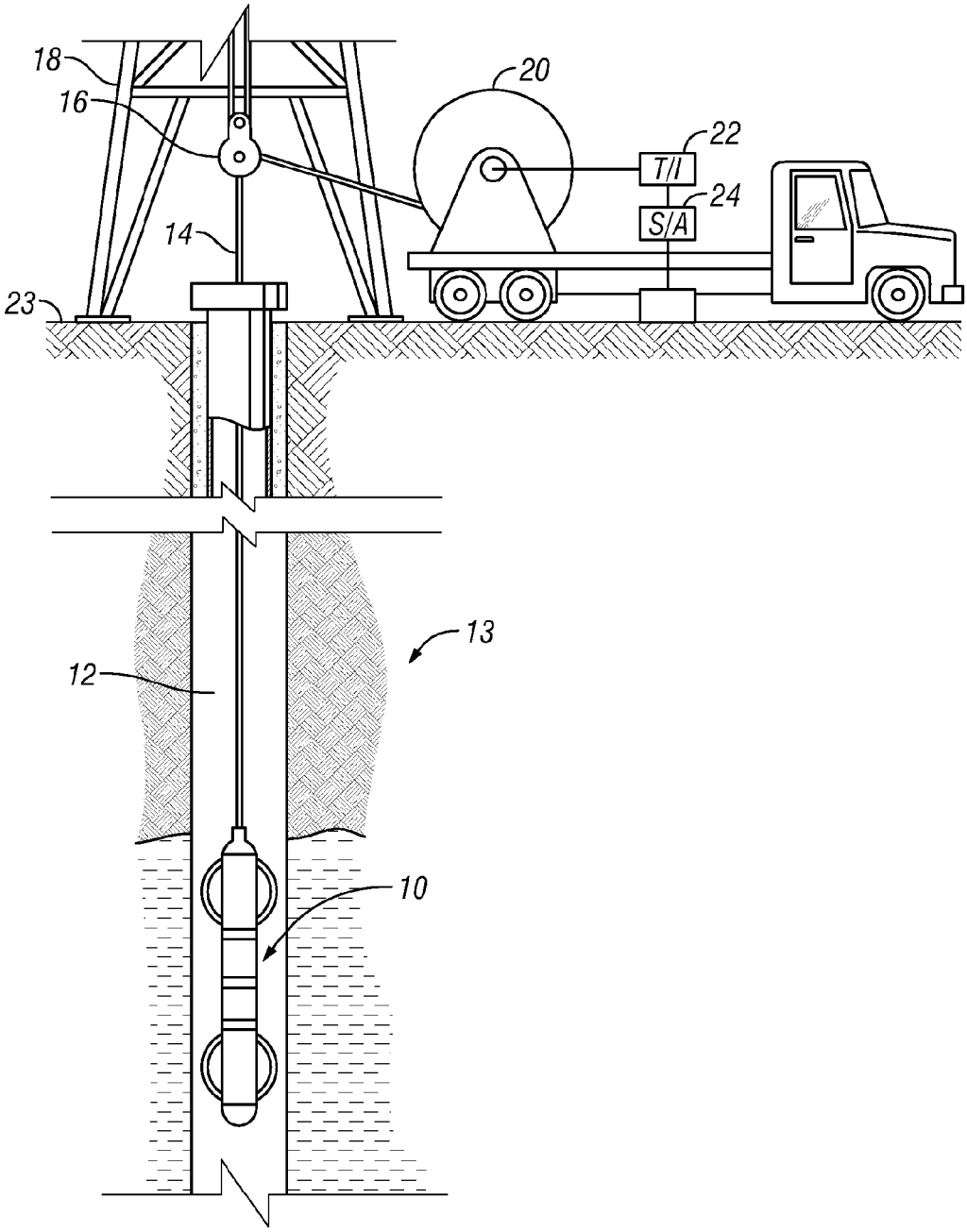
FIG. 1 is a schematic illustration of a wireline logging system.

FIG. 1 shows a logging tool 10 suspended in a borehole 12 that penetrates earth formations such as 13, from a suitable cable 14 that passes over a sheave 16 mounted on drilling rig 18. By industry standard, the cable 14 includes a stress member and seven conductors for transmitting commands to the tool and for receiving data back from the tool as well as power for the tool. The tool 10 is raised and lowered by draw works 20. Electronic module 22, on the surface 23, transmits the required operating commands downhole and in return, receives data back which may be recorded on an archival storage medium of any desired type for concurrent or later processing. The data may be transmitted in analog or digital form. Data processors such as a suitable computer 24, may be provided for performing data analysis in the field in real time or the recorded data may be sent to a processing center or both for post processing of the data.

Figure 2A:
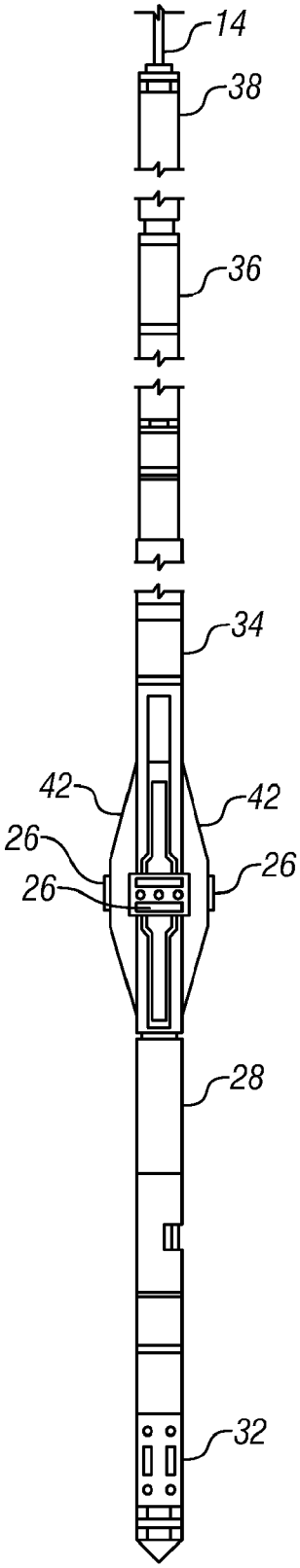
FIG. 2A is an illustration of a logging tool according to the present invention within a cased borehole with poor cementing.

FIG. 2A is a schematic external view of a borehole system according to the present invention. The tool 10 comprises the arrays 26 and is suspended from cable 14. Electronics modules 28 and 38 may be located at suitable locations in the system and not necessarily in the locations indicated. The components may be mounted on a mandrel 34 in a conventional well-known manner. In an exemplary assembly, the outer diameter of the assembly is about 5 inches and about fifteen feet long. An orientation module 36 including a magnetometer and an accelerometer or inertial guidance system may be mounted above the imaging assemblies 26 and 32. The upper portion 38 of the tool 10 contains a telemetry module for sampling, digitizing and transmission of the data samples from the various components uphole to surface electronics 22 (FIG. 1) in a conventional manner. If acoustic data are acquired, they are preferably digitized, although in an alternate arrangement, the data may be retained in analog form for transmission to the surface where it is later digitized by surface electronics 22.

Figure 2B:
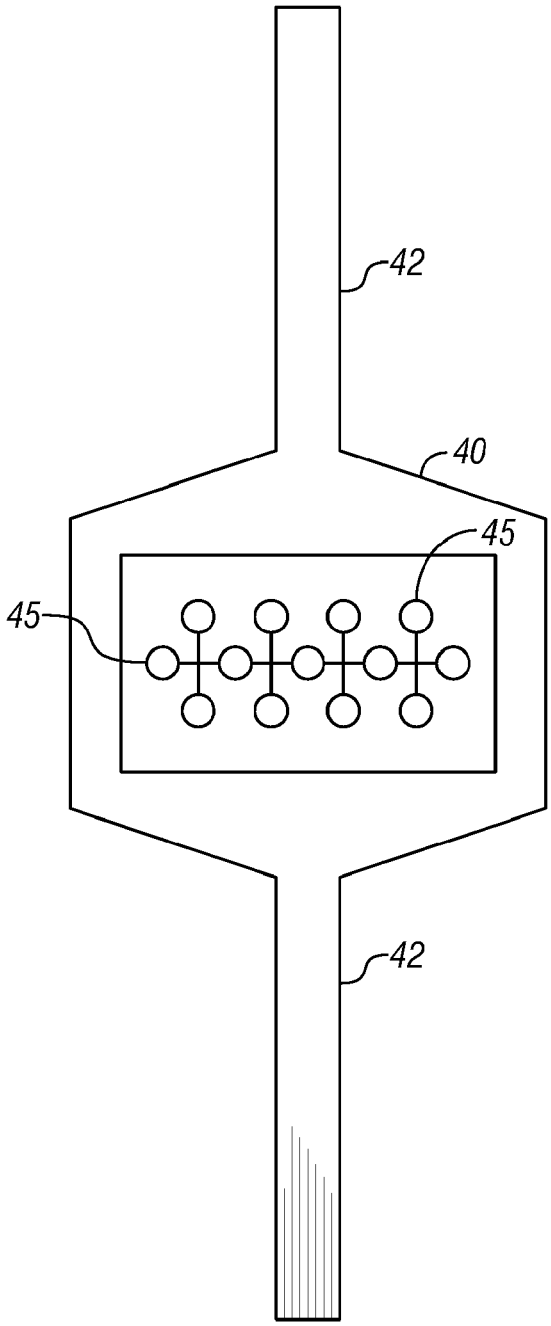
FIG. 2B shows an exemplary pad containing an array of transducers capable of performing the method of the present disclosure.

FIG. 2B shows an exemplary pad containing transducers capable of performing the method of the present disclosure. Pad 40 includes one or more acoustic sensors 45. In one embodiment of the invention, the acoustic sensors comprise electromagnetic acoustic transducers (EMATS) assembled in a pattern to obtain measurements of ultrasonic velocities for the purpose of determining a stress on a material. The pad 40 is attached to the mandrel 34 of FIG. 2A by way of supports 42. The pattern of EMATS shown in FIG. 2B is only an example of many possible configurations that may be used.

In another embodiment of the invention, the sensors may be disposed on two or more vertically spaced apart pads. Such an arrangement makes it easier to make axial measurements as a described below.

The present disclosure generally uses orthogonal acoustic velocity measurements in the steel tubulars to determine in-situ stress. In one possible embodiment, the velocity of a vibrational (acoustic) wave traveling axially in a casing is compared to the velocity of a similar wave traveling circumferentially at substantially the same point in the casing. Differences in the resulting measured velocities indicate either torque or axial stress in the casing. With a more complex arrangement using segmented circumferential or axial measurements, differences in axial stress around the circumference of the casing may indicate bending or crushing loads being applied to the casing by the formation. Also, localized stress measurements made in the area of casing corrosion or mechanical defects can be used to predict potential points of casing rupture. Since the properties of casing steel may vary, the use of orthogonal measurements is critical to identifying changes caused by stress from background changes in materials.

Measurement of acoustic travel time may be substituted with alternative measurements that are affected by casing stress. One alternative measurement might be magnetic permeability. The angle between the two measurements may be something other than orthogonal. A 90° angle, however, maximizes sensitivity of the measurement.

Measurements of stress in casing or tubing downhole have multiple potential uses. These uses potentially include casing deformation, freepoint indicators, and formation stresses (as transferred to the casing). The disclosed method offers a potential method of making an absolute stress measurement in a casing or tubing.

The present disclosure discusses an apparatus and method for performing acoustic testing on a casing or tubular. An ultrasonic wave can be produced at one location on the tubular and the wave can later be detected at the same or another location on the tubular. One way to create ultrasound within a material is via an EMAT. An EMAT comprises a magnetic element, such as a permanent magnet, and a set of wires. In general, the EMAT is placed against the material to be tested such that the set of wires are located between the magnetic element and the material to be tested. When a wire or coil is placed near to the surface of an electrically conducting object and is driven by a current at a desired ultrasonic frequency, eddy currents are induced in a near surface region. If a static magnetic field is also present, these currents experience a Lorentz force of the form $$\vec{F}=\vec{J}\times\vec{B} \tag{1}$$

where $\vec{F}$ is a body force per unit volume, $\vec{J}$ is the induced dynamic current density, and $\vec{B}$ is the static magnetic induction. Thus the Lorentz force converts the electrical energy into a mechanical vibration, which can be used to test the material. Alternatively, EMATs may also be based on the use of magnetostrictive properties of the casing/tubing.

Since no coupling device is used between the EMAT and the tested material, the EMAT can operate without contact at elevated temperatures and in remote locations. Thus EMATs can eliminate errors associated with coupling variation in contact measurements and thereby provide precise velocity or attenuation measurements.

The coil and magnet structure used in an EMAT can be designed to excite complex wave patterns and polarizations. FIGS. 3A-3F shows a number of practical EMAT configurations including a biasing magnet structure, a coil configuration, and resultant forces on the surface of the solid for producing acoustic pulses using EMATS. The configurations of FIGS. 3A, 3B, and 3C excite beams propagating normal to the surface of a half-space and produce, respectively, beams with radial, longitudinal, and transverse polarizations. The configurations of FIGS. 3D and 3E use spatially varying stresses to excite beams propagating at oblique angles or along the surface of a component. These configurations are considered for illustrative purposes although any number of variations on these configurations can be used.

Figure 3A:
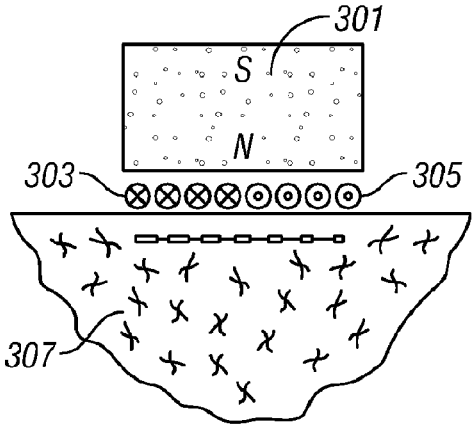
FIGS. 3A-E shows various practical transducer configurations that may be used on a material and resultant forces on the surface of the material for producing acoustic pulses.

FIG. 3A shows a cross-sectional view of a spiral coil EMAT configuration for exciting radially polarized shear waves propagating normal to the surface. Permanent magnet 301 and tubular 307 are separated by a space containing a wire represented by one or more wires as shown as wire segments 303 and 305. The wire segments 303 and 305 represent separate groups of wire segments carrying current in anti-parallel directions in the manner illustrated in FIG. 3A, thereby exciting the radially polarized shear waves propagating normal to the surface.

Figure 3B:
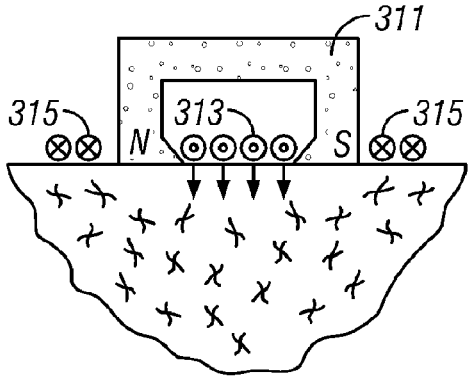

FIG. 3B shows a cross-sectional view of a tangential field EMAT configuration for exciting longitudinally polarized compressional waves propagating normal to the surface. Permanent magnet 311 is placed against tubular to produce a magnetic field parallel to the surface. A magnet such as the magnet 311 of FIG. 3B having a horseshoe configuration may be used. Wires segments 313 provide a current flowing between the magnetic poles perpendicular to the direction of the local magnetic field of magnet 311. Wire segments 315 provide a current flowing anti-parallel to the current in wire segments 313 in a region exterior to the magnetic poles.

Figure 3C:
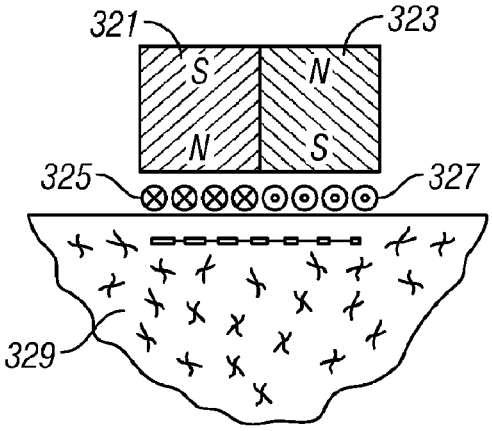

FIG. 3C shows a cross-sectional view of a normal field EMAT configuration for exciting plane polarized shear waves propagating normal to the surface. The configuration comprises a pair of magnets 321 and 323 assembled so as to provide two anti-parallel magnetic fields at the surface of the tubular. The permanent magnets 321 and 323 are separated from tubular 329 by a space containing one or more wires 325 and 327 providing anti-parallel current.

Figure 3D:
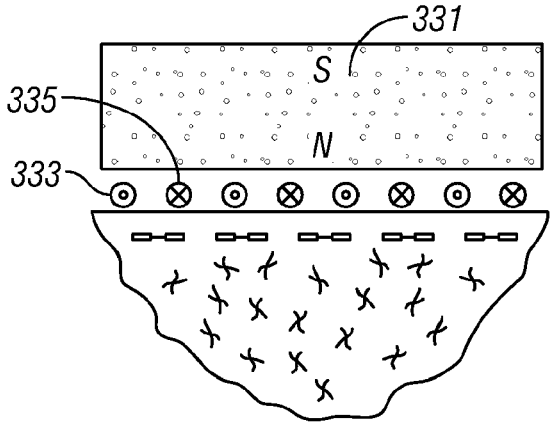

FIG. 3D shows a cross-sectional view of a meander coil EMAT configuration for exciting obliquely propagating L (long) or SV waves, Rayleigh waves, or guided modes (such as Lamb waves) of plates. The configuration includes a permanent magnet and tubular separated by a space containing wire segments such as one or more wires 333 and 335 which provides current flowing in sequentially alternating directions.

Figure 3E:
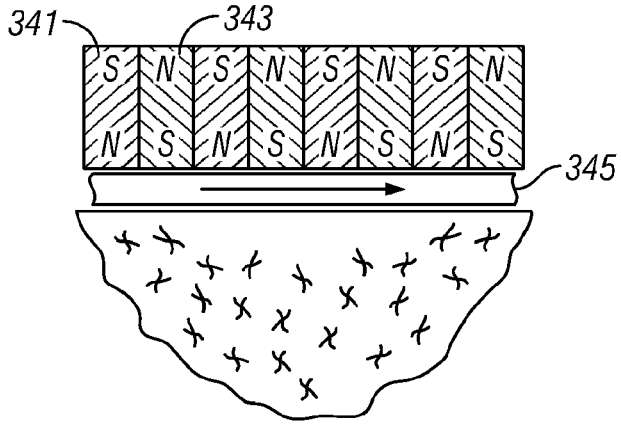

FIG. 3E shows a cross-sectional view of a periodic permanent magnet EMAT for exciting grazing or obliquely propagating horizontally polarized (SH) waves or guided SH modes of plates. Multiple permanent magnets such as magnets 341 and 343 are assembled so as to provide alternating magnetic polarities at the surface of the tubular. The magnetic assembly and tubular are separated by a space containing a wire 345 that provides a current in a single direction.

For sheet and plate specimens experiencing applied or residual stress, the principal stresses $\sigma_a$ and $\sigma_b$ may be inferred from orthogonal velocity measurements. Eq. (2) relates ultrasonic velocities to the principle stresses experienced in a sheet or plate:

$$2\rho V_{avg}[V(\theta)-V(\theta+\pi/2)]=\sigma_a-\sigma_b \tag{2}$$

In Eq. (2), $V_{avg}$ is the average shear velocity and $\rho$ is a density of a material. $V(\theta)$ and $V(\theta+\pi/2)$ are mutually perpendicular wave velocities as can be detected at a transducer. It is understood that velocity difference $V(\theta)-V(\theta+\pi/2)$ is maximized when the ultrasonic propagation directions are aligned with the principal stress axes. The magnitude of this difference, along with the density and mean velocity can be used to estimate the principal stress difference.

Figure 4:
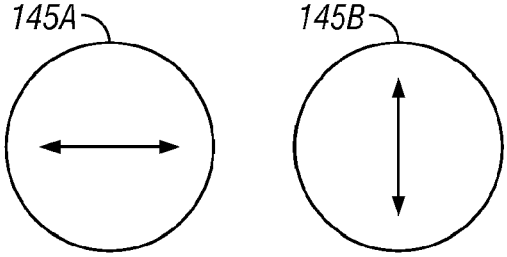
FIG. 4 is a schematic illustrations of two EMATs configured to generate shear-waves in two different directions.

FIG. 4 shows an arrangement of two EMATS 145A and 145B. The pad 40 illustrated and FIG. 2B is not shown. When EMATS 145A and 145B are of the type shown in FIG. 3E, they will produce horizontally polarized shear-wave propagating along the tool axis and circumferential to the tool axis, thus providing the necessary measurements for solving eqn. (2). Those versed in the art would appreciate that using an array of transducers as shown in FIG. 2B, it would be possible to generate horizontally polarized shear waves propagating in different directions. The EMATs, in addition to acting as transmitters, can also act as receivers, so that by having two EMATs with the same polarization at different spatial positions, it is possible to determine the velocity of propagation of the wave. In addition, by having such transducers mounted on different pads on the downhole logging to it is possible to make measurements of the stress differences circumferentially around the borehole.

By using transducers of the type shown in FIG. 3B it would be possible to make measurements of compression velocity at different azimuthal positions along the borehole. Variations in this velocity are indicative of circumferential variations of the stress. The same is true using transducers of the type shown in FIG. 3C. But using transducers of the type shown in FIG. 3D it would be possible to generate Rayleigh waves on land waves along the surface of the tubular.

In addition, those versed in the art would recognize that the velocity of propagation of a vertically polarized shear-wave may differ from the velocity of propagation of the horizontally polarized shear-wave in the same direction. This difference may also be indicative of the stress in the garden. Such measurements may be obtained by using transducers of the type shown in FIGS. 3D and 3E.

In one embodiment a velocity of an acoustic wave traveling axially in the casing is compared to the velocity of a similar wave traveling circumferentially at substantially the same point in the casing. Differences in the measured velocities are indicative of torque or axial stress in the casing. With a more complex arrangement using segmented circumferential or axial measurements made with pad-mounted EMATs, differences in axial stress around the circumference of the casing are indicative of bending a crushing load being applied to the casing by the formation. Localized test measurements made in the area of casing corrosion or mechanical defects are used to predict potential points of casing failure. As would be known to those versed in the art, such casing corrosion or mechanical defects would produce changes in the stress field. All of these use measurements having orthogonal direction of propagation or orthogonal polarization or both. Properties of casings steel may vary, so that the use of such measurements is important in identifying changes caused by stress from changes caused by differences in the steel.

The invention has been described above is a specific example of using EMATS as the acoustic sensors. This is not to be construed as a limitation on the invention. The method of the invention could also be carried out using other side types of sensors such as piezoelectric transducers and wedge transducers. Wedge transducers are discussed, for example, in U.S. Pat. No. 4,593,568 to Telford et al.

The invention has been described above with reference to a device conveyed on a wireline. However the method of invention may also be practices using the tool conveyed on a tubular such as a drillstring or coiled tubing, or on a slickline.

Implicit in the processing method of the present invention is the use of a computer program implemented on a suitable machine readable medium that enables the processor to perform the control and processing. The machine readable medium may include ROMs, EPROMs, EAROMs, Flash Memories and Optical disks. Such a computer program may output the results of the processing, such as the stress constraints, to a suitable tangible medium. This may include a display device and/or a memory device.

What is claimed is:

1. An apparatus configured to evaluate a tubular within a borehole, the apparatus comprising:

a plurality of acoustic transducers configured to generate and receive first and second acoustic waves in a body of the tubular, the second acoustic wave differing from the first acoustic wave in at least one of (A) a direction of propagation, and (B) a direction of polarizations; and a processor configured to determine from a velocity of the first acoustic wave and a velocity of the second acoustic wave an indication of stress in the tubular, wherein the first and second acoustic waves are generated at a substantially similar stress condition of the tubular.

2. The apparatus of claim 1 wherein the acoustic transducers are selected from the group consisting of: (i) electromagnetic acoustic transducers, (ii) piezoelectric transducers, and (iii) wedge transducers.

3. The apparatus claim 1 wherein the plurality of acoustic transducers are disposed on at one least pad extendable from a body of a logging tool.

4. The apparatus of claim 3 wherein the at least one pad comprises a plurality of pads.

5. The apparatus of claim 1 wherein the first acoustic wave comprises a horizontally-polarized shear wave propagating in a first direction, and the second acoustic wave comprises a horizontally-polarized shear waves propagating in a direction substantially orthogonal to the first direction.

6. The apparatus of claim 1 wherein the first acoustic wave comprises a horizontally polarized shear-wave and the second acoustic wave comprises a vertically polarized shear-wave propagating in a direction that is the same as a direction of propagation of the horizontal the polarized shear wave.

7. The apparatus of claim 1 wherein the indication is related to at least one of (i) a torque, (ii) an axial stress, (iii) a bending load, (iv) a crushing load, (v) corrosion of the tubular, and (vi) a mechanical defect in the tubular.

8. The apparatus of claim 2 further comprising a conveyance device configured for conveying the logging tool into the borehole, the conveyance device selected from (i) a wireline, (ii) a drilling tubular, (iii) a slickline, and (iv) coiled tubing.

9. The apparatus of claim 1 wherein the tubular is selected from the group consisting of: (i) production tubing, (ii) casing, and (iii) a drilling tubular.

10. A method of evaluating a tubular within a borehole, the method comprising:

propagating and receiving first and second acoustic waves in a body of the tubular, the second acoustic wave differing from the first acoustic wave in at least one of (A) a direction of propagation, and (B) a direction of polarizations; and determining from a velocity of the first acoustic wave and a velocity of the second acoustic wave an indication of stress in the tubular;

wherein the first and second waves are propagated at a substantially similar stress condition of the tubular.

11. The method of claim 10 further comprising generating the first acoustic wave and the second acoustic wave using a plurality of acoustic transducers disposed on at least pad extendable from a body of a logging tool.

12. The method of claim 11 further comprising disposing the plurality of acoustic transducers on a plurality of pads.

13. The method of claim 10 wherein the first acoustic wave and the second acoustic wave comprise horizontally-polarized shear waves propagating in substantially orthogonal directions.

14. The method of claim 10 wherein the first acoustic wave comprises a horizontally polarized shear-wave and the second acoustic wave comprises a vertically polarized shear-wave propagating in a direction that is the same as a direction of propagation of the horizontal the polarized shear wave.

15. The method of claim 10 wherein the indicator is related to at least one of (i) a torque, (ii) an axial stress, (iii) a bending load, (iv) a crushing load, (v) corrosion of the tubular, and (vi) a mechanical defect in the tubular.

16. The method of claim 10 further comprising conveying the logging tool into the borehole using a conveyance device selected from (i) a wireline, (ii) a drilling tubular, (iii) a slickline, and (iv) coiled tubing.

17. The method of claim 10 wherein the tubular is selected from the group consisting of: (i) production tubing, (ii) casing, and (iii) a drillstring.

18. A computer-readable medium product having stored thereon instructions that when read by a processor, cause the processor to perform a method, the method comprising:

determining an indication of a stress field in a tubular from a velocity of a first acoustic wave and a velocity of second acoustic wave generated and received in a body of the tubular by a plurality of acoustic transducers, the second acoustic wave differing from the first acoustic wave in at least one of: (A) a direction of propagation, and (B) a direction of polarization;

wherein the first and second acoustic waves are generated at a substantially similar stress condition of the tubular.

19. The medium of claim 18 further comprising at least one of (i) a ROM, (ii) an EPROM, (iii) an EEPROM, (iv) a flash memory, and (v) an optical disk.

*20. A non-transitory computer-readable medium product having stored thereon instructions that when read by a processor, cause the processor to perform a method, the method comprising:*

*propagating first and second acoustic waves in a body of a tubular, the second acoustic wave differing from the first acoustic wave in at least one of (A) a direction of propagation, and (B) a direction of polarizations; and*

*determining from a velocity of the first acoustic wave and a velocity of the second acoustic wave an indication of one of: (i) stress and (ii) a mechanical defect in the tubular;*

*wherein the first and second waves are propagated at a substantially similar stress condition of the tubular.*

*21. The non-transitory computer-readable medium product of claim 20 further comprising at least one of (i) a ROM, (ii) an EPROM, (iii) an EEPROM, (iv) a flash memory, and (v) an optical disk.*

*22. An apparatus configured to evaluate a tubular within a borehole, the apparatus comprising:*

*a plurality of acoustic transducers configured to generate and receive first and second acoustic waves in a body of the tubular, the second acoustic wave differing from the first acoustic wave in at least one of (A) a direction of propagation, and (B) a direction of polarizations; and*

*a processor configured to determine from a velocity of the first acoustic wave and a velocity of the second acoustic wave an indication of one of: (i) stress and (ii) a mechanical defect in the tubular,*

*wherein the first and second acoustic waves are generated at a substantially similar stress condition of the tubular.*

*23. The apparatus of claim 22 wherein the acoustic transducers are selected from the group consisting of: (i) electromagnetic acoustic transducers, (ii) piezoelectric transducers, and (iii) wedge transducers.*

*24. The apparatus claim 22 wherein the plurality of acoustic transducers are disposed on at least one pad extendable from a body of a logging tool.*

*25. The apparatus of claim 24 wherein the at least one pad comprises a plurality of pads.*

*26. The apparatus of claim 22 wherein the first acoustic wave comprises a horizontally-polarized shear wave propagating in a first direction, and the second acoustic wave comprises a horizontally-polarized shear wave propagating in a direction substantially orthogonal to the first direction.*

*27. The apparatus of claim 22 wherein the first acoustic wave comprises a horizontally polarized shear-wave and the second acoustic wave comprises a vertically polarized shear-wave propagating in a direction that is the same as a direction of propagation of the horizontally polarized shear wave.*

*28. The apparatus of claim 22 wherein the indication is related to at least one of (i) a torque, (ii) an axial stress, (iii) a bending load, (iv) a crushing load, (v) corrosion of the tubular, and (vi) a mechanical defect in the tubular.*

*29. The apparatus of claim 22 further comprising a conveyance device configured for conveying the logging tool into the borehole, the conveyance device selected from (i) a wireline, (ii) a drilling tubular, (iii) a slickline, and (iv) coiled tubing.*

*30. The apparatus of claim 22 wherein the tubular is selected from the group consisting of: (i) production tubing, (ii) casing, and (iii) a drilling tubular.*

*31. A method of evaluating a tubular within a borehole, the method comprising:*

*propagating first and second acoustic waves in a body of the tubular, the second acoustic wave differing from the first acoustic wave in at least one of (A) a direction of propagation, and (B) a direction of polarization; and*

*determining from a velocity of the first acoustic wave and a velocity of the second acoustic wave an indication of one of: (i) stress and (ii) a mechanical defect in the tubular;*

*wherein the first and second waves are propagated at a substantially similar stress condition of the tubular.*

*32. The method of claim 31 further comprising generating the first acoustic wave and the second acoustic wave using a plurality of acoustic transducers disposed on at least one pad extendable from a body of a logging tool.*

*33. The method of claim 32 further comprising disposing the plurality of acoustic transducers on a plurality of pads.*

*34. The method of claim 31 wherein the first acoustic wave and the second acoustic wave comprise horizontally-polarized shear waves propagating in substantially orthogonal directions.*

*35. The method of claim 31 wherein the first acoustic wave comprises a horizontally polarized shear-wave and the second acoustic wave comprises a vertically polarized shear-wave propagating in a direction that is the same as a direction of propagation of the horizontally polarized shear wave.*

*36. The method of claim 31 wherein the indicator is related to at least one of (i) a torque, (ii) an axial stress, (iii) a bending load, (iv) a crushing load, (v) corrosion of the tubular, and (vi) a mechanical defect in the tubular.*

*37. The method of claim 31 further comprising conveying the logging tool into the borehole using a conveyance device selected from (i) a wireline, (ii) a drilling tubular, (iii) a slickline, and (iv) coiled tubing.*

*38. The method of claim 31 wherein the tubular is selected from the group consisting of: (i) production tubing, (ii) casing, and (iii) a drillstring.*

* * * * *